(12) United States Patent
Torrence (10) Patent No.: US 9,409,846 B2
(45) Date of Patent: Aug. 9, 2016

(54) PROCESS FOR SEPARATING PRODUCT GAS USING CARBONYLATION PROCESSES

(71) Applicant: Celanese International Corporation, Irving, TX (US)

(72) Inventor: G. Paull Torrence, League City, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

(21) Appl. No.: 14/212,836

(22) Filed: Mar. 14, 2014

(65) Prior Publication Data

US 2014/0275620 A1    Sep. 18, 2014

Related U.S. Application Data

(60) Provisional application No. 61/787,913, filed on Mar. 15, 2013, provisional application No. 61/787,940, filed on Mar. 15, 2013.

(51) Int. Cl.
  *C07C 31/08* (2006.01)
  *C07C 51/12* (2006.01)
  *C07C 29/149* (2006.01)

(52) U.S. Cl.
  CPC ............... *C07C 51/12* (2013.01); *C07C 29/149* (2013.01); *Y02P 20/132* (2015.11)

(58) Field of Classification Search
  CPC .......... C07C 31/08; C07C 51/12; C07C 53/68
  USPC .......................................... 568/885; 562/519
  See application file for complete search history.

(56) References Cited

U.S. PATENT DOCUMENTS

| | | | |
|---|---|---|---|
| 4,242,875 A | 1/1981 | Schaefer | |
| 4,255,591 A | 3/1981 | Makin et al. | |
| 4,727,200 A | 2/1988 | Wegman et al. | |
| 4,756,730 A | 7/1988 | Stupin | |
| 4,994,608 A | 2/1991 | Torrence et al. | |
| 5,511,382 A | 4/1996 | Denis et al. | |
| 5,659,077 A | 8/1997 | McFarlan | |
| 5,840,969 A | 11/1998 | Joensen | |
| 5,917,089 A | 6/1999 | Howard | |
| 6,248,796 B1 | 6/2001 | Jackson et al. | |
| 6,303,813 B1 | 10/2001 | Scates et al. | |
| 6,596,781 B1 | 7/2003 | Schinski | |
| 6,685,754 B2 | 2/2004 | Kindig et al. | |
| 6,753,353 B2 | 6/2004 | Jackson et al. | |
| 7,196,239 B2 | 3/2007 | Van Egmond et al. | |
| 7,498,016 B2 | 3/2009 | Thiebaut | |
| 7,678,939 B2 * | 3/2010 | Torrence ........................ 562/607 | |
| 7,718,832 B1 | 5/2010 | Hurley et al. | |
| 7,842,844 B2 | 11/2010 | Atkins | |
| 7,863,489 B2 | 1/2011 | Johnston et al. | |
| 7,884,253 B2 | 2/2011 | Stites et al. | |
| 7,947,116 B2 | 5/2011 | Mundschau et al. | |
| 8,080,693 B2 | 12/2011 | Chornet et al. | |
| 8,088,832 B2 | 1/2012 | Melnichuk et al. | |
| 8,137,655 B2 | 3/2012 | Chornet et al. | |
| 8,142,530 B2 | 3/2012 | Klepper et al. | |
| 8,288,594 B2 | 10/2012 | Stites et al. | |
| 8,436,215 B2 | 5/2013 | Chornet et al. | |
| 8,502,001 B2 | 8/2013 | Daniel et al. | |
| 8,569,551 B2 | 10/2013 | Jevtic et al. | |
| 2011/0046421 A1 | 2/2011 | Daniel et al. | |
| 2011/0224462 A1 | 9/2011 | Ditzel et al. | |
| 2012/0078012 A1 | 3/2012 | Torrence et al. | |
| 2012/0083623 A1 | 4/2012 | Hokkanen et al. | |
| 2012/0253084 A1 * | 10/2012 | Grusendorf et al. ........... | 568/884 |
| 2013/0046032 A1 | 2/2013 | Scates et al. | |
| 2013/0046119 A1 | 2/2013 | Scates et al. | |
| 2013/0046120 A1 | 2/2013 | Zink et al. | |

FOREIGN PATENT DOCUMENTS

| | | |
|---|---|---|
| CN | 101439256 | 5/2009 |
| CN | 101805242 | 8/2010 |
| CN | 102229520 | 11/2011 |
| CN | 102530857 | 7/2012 |
| CN | 103359732 | 10/2013 |
| EP | 0104197 | 4/1984 |
| EP | 0137749 | 4/1985 |
| EP | 0167300 | 1/1986 |
| EP | 2060553 | 5/2009 |
| EP | 2072486 | 6/2009 |
| RU | 1823423 A1 | 8/1996 |
| WO | WO 83/03409 | 10/1983 |
| WO | WO 03/097523 | 11/2003 |
| WO | WO 2006/005269 | 1/2006 |

OTHER PUBLICATIONS

Ilias, "Separation of Hydrogen and Carbon Dioxide Using a Novel Membrane Reactor in Advanced Fossil Energy Conversion Process", 2002, 13 pages.

Subramani et al., "A Review of Recent Literature to Search for an Efficient Catalytic Process for the Conversion of Syngas to Ethanol," Energy & Fuels, 2008, vol. 22, pp. 814-839.

Tempesti, et al., "Carboxylic acids by methanol carbonylation with syngas using polymer-supported rhodium catalysts", Reactive and Functional Polymers, 33, 1997, pp. 211-216.

Torrence, "Carbon Monoxide Production and Purification Technologies", Chem Systems, 1998.

Winter, "Make ethanol via syngas", Hydrocarbon Processing, 1986, pp. 71-73.

International Search Report and Written Opinion for PCT/US2014/027984 mailed Oct. 15, 2014.

Patent Cooperation Treaty, Third Party Observation, PCT Application No. PCT/US2014/027984 mailed May 11, 2015.

* cited by examiner

*Primary Examiner* — Sikarl Witherspoon
(74) *Attorney, Agent, or Firm* — Kilpatrick Townsend & Stockton LLP (57) ABSTRACT

The present invention is related to separating product gas using a carbonylation reactor in which the carbon monoxide is consumed to produce acetic acid, and hydrogen and carbon dioxide are recovered. The recovered hydrogen may be further purified to reduce the concentration of carbon oxides. The present invention provides improved methods for converting product gas or syngas to ethanol.

8 Claims, 2 Drawing Sheets

PROCESS FOR SEPARATING PRODUCT GAS USING CARBONYLATION PROCESSES

PRIORITY CLAIM

The present invention claims priority to U.S. App. Nos. 61/787,913 and 61/787,940, both filed Mar. 15, 2013, the entire contents and disclosure of which are hereby incorporated by reference.

FIELD OF THE INVENTION

The present invention relates generally to separating product gas or syngas using a carbonylation process. The product gas contains carbon monoxide, carbon dioxide, and hydrogen, and may be separated by reacting the carbon monoxide during the carbonylation process and recovering the hydrogen. For further integration, in one embodiment, the recovered hydrogen and acetic acid produced may be fed together to a hydrogenation reactor to produce ethanol.

BACKGROUND OF THE INVENTION

Synthesis gas ("syngas") is a gas mixture comprising primarily carbon monoxide hydrogen of varying amounts and with some carbon dioxide. Syngas is widely used as a reactant for industrial chemicals. There are a variety of methods to purify syngas to produce different product purities of carbon monoxide and hydrogen. Syngas separation is energy intensive and one of the most expensive process steps to obtain pure hydrogen and carbon monoxide for industrial use. Cryogenic purification is widely used to separate syngas as described in U.S. Pat. Nos. 5,511,382, 4,756,730, and 4,242,875. One problem in producing pure hydrogen and carbon monoxide streams is that the separation is energy intensive. The presence of additional gases, such as nitrogen and methane, may further increase the energy requirements for separation. Also, the complexity of the purification process is dependent on the desired purity of the carbon monoxide and hydrogen.

Some conventional processes have used syngas directly in producing industrial chemicals, as described in U.S. Pat. No. 6,596,781, which shows using syngas for a Fischer-Tropsch process to produce diesel, and syngas for producing methanol using a copper and/or zinc catalyst. Methanol synthesis may be highly selective, but the process consumes both hydrogen and carbon dioxide from the syngas to produce methanol. Although there may be effluent gas from the methanol synthesis process, the composition may vary depending on the hydrogen to carbon monoxide ratio of the syngas and selectivity to methanol. Thus, these processes cannot separate syngas.

Various processes have been described for producing acetic acid from syngas. For example, U.S. Pat. No. 8,088,832 describes a method for synthesizing ethanol using synthetic routes via syngas. A method and apparatus for gasifying biomass in a steam gasifier that employs a fluidized bed and heating using hot flue gases from the combustion of syngas is described. Methods and apparatus for converting syngas into ethanol are also disclosed, using stepwise catalytic reactions to convert the carbon monoxide and hydrogen into ethanol using catalysts including iridium acetate. The stepwise catalyst reaction converts methanol, carbon monoxide, and hydrogen into a mixture comprising methyl acetate, hydrogen, methanol, acetic acid, and water. Hydrogen and methyl acetate are separated from the mixture and used in the ethanol production.

U.S. Pat. No. 8,080,693 describes processes for converting methanol to ethanol by reacting methanol and carbon monoxide in the presence of a catalyst to produce a product having at least 25 mole % methyl acetate and, in some instances, acetic acid. The acetic acid is then reacted with at least one alcohol to produce at least one acetate selected from methyl acetate, ethyl acetate, and butyl acetate. The at least one acetate and the methyl acetate produced as a result of reacting methanol and carbon monoxide then are hydrogenated to produce ethanol. Syngas may be produced from biomass to produce all or a portion of the methanol, hydrogen, and carbon monoxide requirements for the process. Hydrogen is separated from the syngas prior to the carbonylation reactor. A hydrogen permeable membrane is described for producing a carbon monoxide stream having less than 5 mol. % hydrogen.

U.S. Pat. No. 7,498,016 describes a method for the production of syngas from methanol feedstock. The methanol feed is supplied to a partial oxidation reactor with oxygen and optionally steam to yield a mixed stream of hydrogen, carbon monoxide, and carbon dioxide. The carbon dioxide is separated out and the hydrogen and carbon monoxide mixture is fed to a cold box where it is separated into hydrogen-rich and carbon monoxide-rich streams. The separated carbon dioxide can be recycled back to the partial oxidation reactor as a temperature moderator if desired. The carbon monoxide-rich stream can be reacted with methanol in an acetic acid synthesis unit by a conventional process to produce acetic acid or an acetic acid precursor. Optionally, an ammonia synthesis unit and/or vinyl acetate monomer synthesis unit can be integrated into the plant.

U.S. Pat. No. 6,596,781 describes an integrated process for carrying out the production of Fischer-Tropsch products and acetic acid made using the methanol and carbonylation route which uses the hydrogen recovered from the methanol production to upgrade the Fischer-Tropsch products.

U.S. Pat. No. 5,659,077 describes an integrated process for production of acetic acid that involves subjecting a feed mixture consisting of (a) methane gas and (b) gaseous oxygen, air, or a mixture thereof, to partial oxidation without production of syngas in a reaction zone at elevated temperature and pressure to form a reaction mixture containing methanol, carbon monoxide, carbon dioxide, methane and water vapor. At least a portion of the water vapor is removed from the reaction mixture, and the remaining partial oxidation reaction mixture is fed, together with additional methanol from an external source, through a carbonylation reaction zone at elevated temperature and pressure to form a reaction product containing acetic acid and/or methyl acetate and methanol. The additional methanol is added in an amount such that the additional methanol together with the methanol produced by partial oxidation is sufficient to convert substantially all of the carbon monoxide produced by partial oxidation. Excess methane and carbon dioxide are recycled from the carbonylation reaction zone back to the partial oxidation reaction zone, and methanol in the carbonylation reaction product is recycled back to the carbonylation reaction zone and acetic acid and/or methyl acetate is recovered as product.

WO2003097523 describes a process that produces both methanol and acetic acid under substantially stoichiometric conditions, wherein an unadjusted syngas having an R ratio less than 2.0 is provided. All or part of the unadjusted syngas is supplied to a separator unit to recover $CO_2$, CO and hydrogen. At least a portion of any one or combination of the recovered $CO_2$, CO and hydrogen is added to any remaining syngas not so treated or alternatively combines in the absence of any remaining unadjusted syngas to yield an adjusted syngas with an R ratio of 2.0 to 2.9 which is used to produce methanol. Any recovered $CO_2$ not used to adjust the R ratio of the unadjusted syngas can be supplied to the reformer to enhance CO production. At least a portion of the recovered CO is reacted in the acetic acid reactor with at least a portion of the produced methanol to produce acetic acid or an acetic acid precursor by a conventional process.

Other processes describe converting syngas to ethanol. U.S. Pat. No. 7,718,832 describes a catalytic process that selectively produces ethanol by contacting syngas, composed primarily of hydrogen and carbon monoxide, with three catalysts within a reactor. The first catalyst is a hydrogenation promoter comprising Cu—Zn, Mo or Fe with an optional alkali metal additive and an optional support of aluminum oxide, silica, zeolite or clay. The second catalyst is a homologation promoter comprising one or more of the Group VIII metals in free or combined form with a co-catalyst metals consisting of Y or lanthanide or actinide series metals with optional additives and support. The third catalyst is a hydrogenation promoter.

U.S. Pat. No. 7,842,844 describes a process for the conversion of hydrocarbons to $C_2$ oxygenates, and uses a conventional catalyst to hydrogenate the $C_2$ oxygenate feed. Hydrocarbons are converted to ethanol and optionally acetic acid by converting hydrocarbon in a syngas reactor into a stream A comprising a mixture of carbon oxide(s) and hydrogen preferably having a $H_2$/CO molar ratio between 1.5 and 2.5, converting at least part of stream A in the presence of a particulate catalyst in a reactor under a temperature between 150 and 400° C. and a pressure of 5 to 200 bar, into a $C_2$-oxygenates stream B, where stream B includes water, alkanes, ethanol, acetaldehyde, ethyl acetate and acetic acid, which together represent at least 80% by weight of the products obtained from the $C_2$-oxygenates conversion reactor. The $C_2$-oxygenates stream B is separated into a stream C comprising $H_2$, CO, $CO_2$ and alkanes, and a stream D including 15 to 40 wt. % acetic acid, 10 to 40 wt. % acetaldehyde and 15 to 40 wt. % ethanol. At least part of stream D is hydrogenated in a hydrogenation reactor into an ethanol stream E, and stream E is subjected to a separating step, followed by recovery of ethanol.

U.S. Pat. No. 8,502,001 describes a process for the production of ethanol from a carbonaceous feedstock, wherein the carbonaceous feedstock is first converted to syngas which is then converted to ethanoic acid, which is then subject to a two stage hydrogenation process by which at least a part of the ethanoic acid is converted by a primary hydrogenation process to ethyl ethanoate, which ethyl ethanoate is converted by a secondary hydrogenation process to produce ethanol.

EP02060553 describes a process for converting hydrocarbons to ethanol involving converting the hydrocarbons to ethanoic acid and hydrogenating the ethanoic acid to ethanol. The stream from the hydrogenation reactor is separated to obtain an ethanol stream and a stream of acetic acid and ethyl acetate, which is recycled to the hydrogenation reactor.

Thus what is needed is a process for separating syngas that significantly reduces capital costs and is energy efficient.

SUMMARY OF THE INVENTION

In a first embodiment, the present invention relates to processes for producing acetic acid comprising converting a carbon source to a product gas comprising carbon monoxide, hydrogen, and carbon dioxide, introducing the product gas and at least one reactant selected from the group consisting of methanol, methyl acetate, methyl formate, dimethyl ether and mixtures thereof to a reactor comprising a reaction medium comprising a catalyst, methyl acetate, promoter, and catalyst stabilizer under carbonylation conditions effective to produce acetic acid, withdrawing a vent gas from the reactor comprising hydrogen and carbon dioxide, withdrawing a reaction solution from the reactor, and recovering acetic acid from the reaction solution. The reaction medium may also comprise a finite amount of water for producing acetic acid.

In a second embodiment, the present invention relates to processes for producing acetic acid comprising introducing a product gas comprising carbon monoxide, hydrogen, and carbon dioxide and at least one reactant selected from the group consisting of methanol, methyl acetate, methyl formate, dimethyl ether and mixtures thereof to a reactor comprising a reaction medium comprising a catalyst, methyl acetate, promoter, and catalyst stabilizer under carbonylation conditions effective to produce acetic acid, withdrawing a vent gas from the reactor, provided that the carbon monoxide partial pressure in the reactor is less than 15 atm to maintain a carbon monoxide content in the vent gas of less than 40 mol. %, preferably less than 20 mol. %, withdrawing a reaction solution from the reactor, and recovering acetic acid from the reaction solution. The product gas may have a molar ratio of hydrogen to carbon monoxide from 0.2:1 to 6:1. The product gas may have a carbon dioxide to carbon monoxide molar ratio from 1:0.5 to 1:80. The product gas may comprise from 9 mol. % to 80 mol. % hydrogen, from 3 mol. % to 90 mol. % carbon monoxide, and from 0.5 mol. % to 25 mol. % carbon dioxide. The carbon monoxide partial pressure in the reactor may be from 0.3 atm to 15 atm. The hydrogen partial pressure in the reactor may be from 3 atm to 40 atm. The carbon monoxide partial pressure in the reactor may be less than hydrogen partial pressure in the reactor. The vent gas may comprise from 5 mol. % to 95 mol. % hydrogen, and from 4 mol. % to 70 mol. % carbon dioxide, and from 0.2 mol. % to 40 mol. % carbon monoxide.

In a third embodiment, the present invention relates to processes for producing ethanol, by feeding a gas stream having a $H_2$:CO molar ratio of 0.2:1 to 6:1 and at least one reactant selected from the group consisting of methanol, methyl acetate, methyl formate, dimethyl ether and mixtures thereof to a carbonylation reactor in the presence of a first catalyst and a finite amount of water under conditions effective to form a crude product comprising acetic acid and at least one non-condensable gas, and optionally removing a first vent gas comprising hydrogen from the first reactor, separating the crude product to yield an acetic acid product and a second vent stream comprising the at least one non-condensable gas, recovering a hydrogen-enriched stream from at least one of the first vent stream or the second vent stream, and feeding the hydrogen-enriched stream and the acetic acid product to a hydrogenation reactor in the presence of a second catalyst to produce ethanol. The crude product may comprise from 0.1 wt. % to 5 wt. % of a mixture of ethanol and propionic acid. The process may further comprise treating the vent stream to reduce carbon monoxide content. The gas stream may comprise carbon dioxide in an amount from 0.5 mol. % to 25 mol. %. The process may further comprise removing carbon dioxide from the gas stream prior to feeding into the carbonylation reactor. The hydrogen-enriched stream may further comprise less than 0.1 mol. % of carbon monoxide and less than 5 mol. % of carbon dioxide. The first catalyst may be different than the second catalyst and the first catalyst comprises iridium, rhodium, or mixtures thereof. The crude product may comprise less than 25 mol. % methyl acetate.

In a fourth embodiment, the present invention relates to processes for producing ethanol by feeding a gas stream having a $H_2$:CO molar ratio of 0.2:1 to 6:1 and at least one reactant selected from the group consisting of methanol, methyl acetate, methyl formate, dimethyl ether and mixtures thereof to a carbonylation reactor in the presence of a first catalyst and a finite amount of water under conditions effective to form a crude product comprising acetic acid and at least one non-condensable gas, and removing a first vent gas comprising hydrogen from the first reactor, separating the crude product to yield an acetic acid product, recovering a hydrogen-enriched stream from the first vent stream, and feeding the hydrogen-enriched stream and the acetic acid product to a hydrogenation reactor in the presence of a second catalyst to produce ethanol. The vent gas may comprise from 9 mol. % to 80 mol. % hydrogen, from 3 mol. % to 90 mol. % carbon monoxide, and from 0.5 mol. % to 25 mol. % carbon dioxide. The carbon monoxide partial pressure in the reactor may be from 0.3 atm to 15 atm. The hydrogen-enriched stream may further comprise less than 0.1 mol. % of carbon monoxide and less than 5 mol. % of carbon dioxide.

BRIEF DESCRIPTION OF DRAWINGS

The invention may be more completely understood in consideration of the following detailed description of various embodiments of the invention in connection with the accompanying drawings, wherein like numerals designate similar parts.

DETAILED DESCRIPTION OF THE INVENTION

Introduction

Generally, the present invention is related to separating product gas or syngas using a carbonylation reactor in which the carbon monoxide is consumed to produce acetic acid, and hydrogen is recovered. The recovered hydrogen may be further purified to reduce the concentration of carbon oxides. It is surprising and unexpected that feeding a product gas or syngas with a large amount of hydrogen would not cause problems in the carbonylation process, such as decreased acetic acid production efficiency or significant increased impurities.

For purposes of the present invention, the terms "product gas" and "syngas" generally refer to streams comprising hydrogen and carbon monoxide. Product gas is generally used to refer to a stream that further comprises carbon dioxide, i.e. there has been no removal of carbon dioxide from the gas exiting the gasifier. Although syngas may have some carbon dioxide, the carbon dioxide is generally removed from the product gas to produce syngas. In certain situations, these terms may be used interchangeably.

In one embodiment, the recovered hydrogen may be further purified to reduce the concentration of carbon oxides. The recovered hydrogen and produced acetic acid are co-fed to an integrated hydrogenation unit to produce ethanol. Advantageously, the embodiments of the present invention provide improved methods for converting syngas to ethanol.

As described herein, the product gas or syngas is fed to a carbonylation reactor to separate hydrogen and carbon monoxide. Carbon monoxide is consumed in the carbonylation reactor at efficiencies of greater than 90%, e.g., greater than 95% or greater than 97%. Because hydrogen, and carbon dioxide if present, is not required for the carbonylation, substantially all of the hydrogen, and optional carbon dioxide, from the product gas or syngas may pass through the carbonylation reactor and may be subsequently recovered in reactor vent gases. The hydrogen may be used for other products, such as hydrogenating the produced acetic acid to ethanol. Advantageously, the present invention separates the product gas by consuming carbon monoxide and recovering hydrogen.

Figure 1:
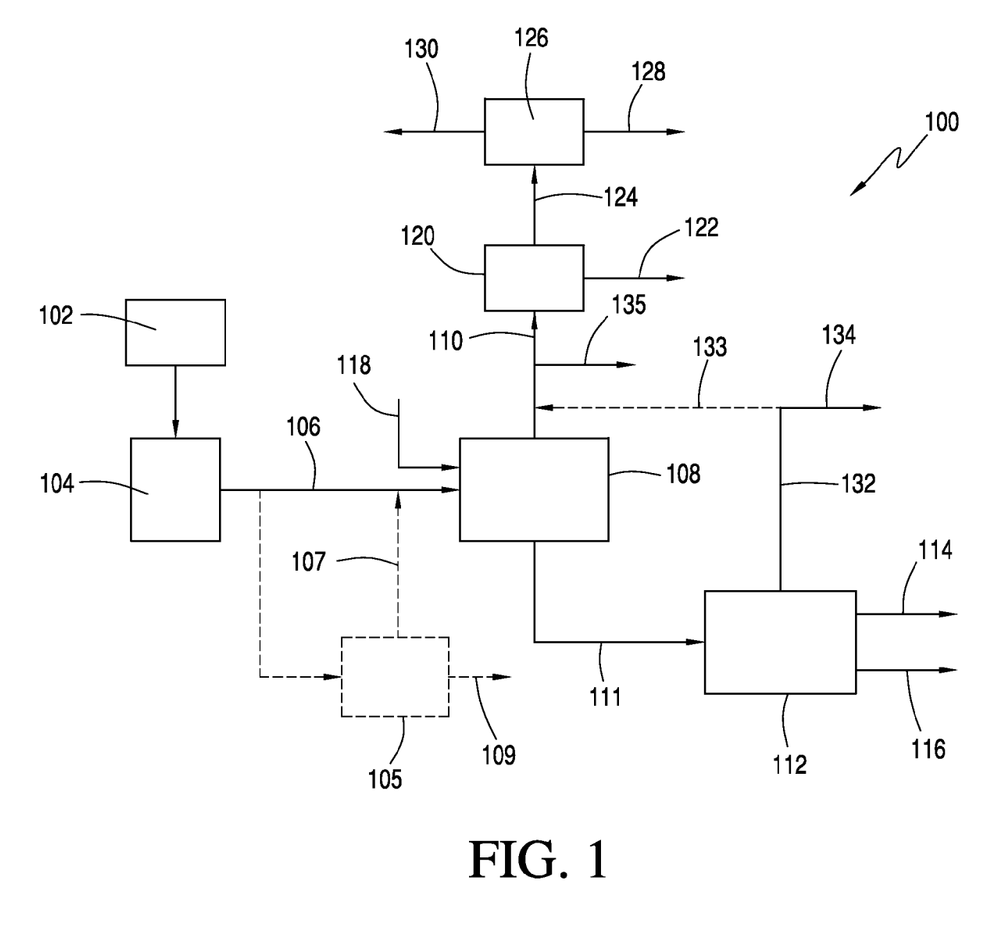
FIG. 1 is a flow diagram of separating product gas using a carbonylation reactor in accordance with one embodiment of the present invention.

In general, process 100, as shown in FIG. 1, involves converting carbon source 102 in a syngas reactor 104 to a product gas 106 that is introduced to a carbonylation reactor 108. A reactor vent gas 110 is withdrawn from carbonylation reactor 108, and treated as described below to recover hydrogen. The carbon monoxide in product gas 106 is converted to acetic acid and/or acetic anhydride and recovered from the distillation and purification unit 112. Depending on the purification, the acetic acid may be recovered with impurities in line 114, such as aldehydes and/or propanoic acid, or recovered as purified acetic acid in line 116.

Product Gas

For purposes of this invention, product gas 106 refers to the effluent exiting the syngas reactor 104, wherein the effluent contains hydrogen, carbon monoxide and carbon dioxide. Thus, there is no requirement that the product must be separated using known separation techniques such as cryogenic separation to produce separate hydrogen and carbon monoxide streams. Instead, the present invention advantageously shifts the separation of the hydrogen and carbon monoxide to the carbonylation reactor 108. This reduces the need for additional processing of product gas 106 prior to the carbonylation reaction. Also, because carbonylation processes have high carbon monoxide conversion, such as greater than 90%, preferably greater than 95% and more preferably greater than 97%, the resulting reactor vent gas may be enriched in hydrogen.

In one embodiment, product gas 106 comprises from 9 mol. % to 80 mol. % hydrogen, e.g., from 10 to 75 mol. %, from 15 to 75 mol. % or from 20 to 60 mol. %. In one embodiment, the product gas comprises from 3 mol. % to 90 mol. % carbon monoxide, e.g., from 25 to 80 mol. % or from 30 to 60 mol. %.

As described herein, the product gas may also comprise carbon dioxide. Because carbon dioxide is not required for carbonylation, it is not necessary to remove carbon dioxide prior to carbonylation. Carbon dioxide, similar to hydrogen, may be recovered in the vent gas. In one embodiment, the product gas comprises from 0.5 mol. % to 25 mol. % carbon dioxide, e.g., from 2 to 15 mol. % or from 5 to 10 mol. %. When carbon dioxide is removed from the product gas, the stream may comprise primarily hydrogen and carbon monoxide. This stream is referred to as syngas for purposes of the present invention.

The product gas has a hydrogen to carbon monoxide molar ratio of 0.2:1 to 6:1, e.g., from 0.6:1 to 4:1, or from 1:1 to 3:1. The product gas also has a carbon dioxide to carbon monoxide molar ratio from 1:0.5 to 1:80, e.g. from 1:2 to 1:20. Process vent/purge streams containing carbon dioxide may also be recycled to the syngas reactor to use the water gas shift reaction (WGSR) to further convert carbon dioxide to carbon monoxide to enhance the carbon efficiency in the carbonylation process.

Contaminants in the carbon source, such as a sulfur, nitrogen, phosphorus and arsenic, are preferably removed from the carbon source prior to feeding the carbon source to the syngas reactor or may be removed from the product gas, depending on the type of carbon source, using well known processes such as a guard beds. The product gas is preferably substantially free of these contaminants.

Figure 2:
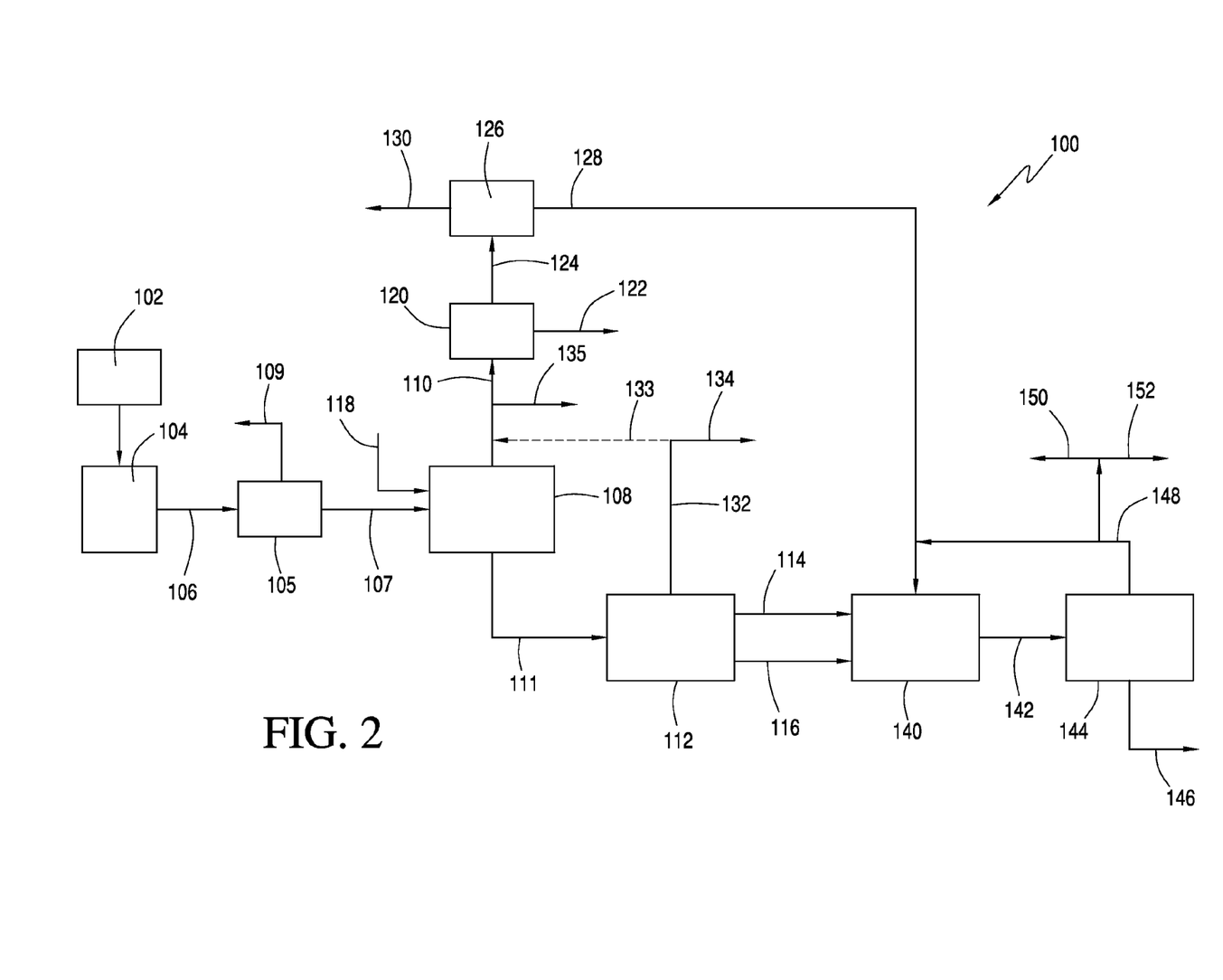
FIG. 2 is a flow diagram of separating syngas using a carbonylation reactor and integrated with a hydrogenation process in accordance with one embodiment of the present invention.

As shown in FIG. 2, carbon dioxide may be removed from product gas 106 acid gas removal device 105 to yield syngas 107. In one embodiment, syngas 107 comprises from 9 mol. % to 80 mol. % hydrogen, e.g., from 10 to 80 mol. %, from 15 to 75 mol. % or from 20 to 60 mol. %. In one embodiment, the syngas comprises from 3 mol. % to 90 mol. % carbon monoxide, e.g., from 25 to 80 mol. % or from 30 to 60 mol. %. The syngas has a hydrogen to carbon monoxide molar ratio of 0.2:1 to 6:1, e.g., from 0.6:1 to 4:1, or from 1:1 to 3:1.

Syngas Reactor

Product gas 106 and highly purified syngas 107 may be produced from a variety of carbon sources 102, including coal, natural gas, petroleum, and biomass. Suitable biomass sources include but are not limited to agricultural plant waste, plant waste from industrial processes, consumer waste and energy crops grown specifically for fuel production. Examples of biomass include, but are not limited to, agricultural wastes, forest products, grasses, and other cellulosic material, timber harvesting residues, softwood chips, hardwood chips, mixtures of softwood and hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, grape seeds, almond shells, pecan shells, coconut shells, coffee grounds, grass pellets, hay pellets, wood pellets, cardboard, paper, plastic, cloth, forest residue, paper mill waste, including sludge and plastics, willow, alfalfa, pelletized refuse derived fuel, bagasse, California highway clippings, and mixtures thereof.

Syngas reactor 104 may be a steam reforming, partial oxidation, gasification, or combination of these reactors. If necessary, the carbon source may be pre-treated prior to being fed to the syngas reactor. Pre-treatments may include pulverization, carbonization and/or torrefaction. These pre-treatments may be necessary when using biomass.

In addition to the carbons source 102, an oxygen stream may be fed to syngas reactor 104. For purposes of the present invention, it is preferred that the oxygen stream comprises at least 50 vol. % oxygen, e.g., at least 75 vol. % oxygen or at least 90 vol. % oxygen. The oxygen stream preferably is substantially free of nitrogen. Hence, the oxygen preferably is not delivered to the syngas reactor in the form of air. In one embodiment, the oxygen stream may contain less than 5 vol. % or less than 1 vol. % nitrogen. Nitrogen may be eliminated by using an air separation unit (ASU) to produce the oxygen stream. ASU uses cryogenic distillation for high-throughput and high-purity oxygen demands. Suitable ASU's provide an oxygen stream having a purity that is greater than 99 vol. % oxygen. In addition, the other gases that are separated, such as nitrogen, may be used as inert gases in an integrated process. ASU's are described in U.S. Pat. Nos. 6,425,937 and 6,889,524, the entire contents and disclosures of which are hereby incorporated by reference. Although the ASU may require increased capital and operating costs, using an oxygen stream may allow operation of a lower temperature gasifier. Other oxygen supply systems such as pressure swing adsorption (PSA) or polymeric membrane systems may also be used.

The syngas reactor may be operated at a temperature from 250° C. to 1200° C., e.g., from 300° C. to 800° C. The pressure of the syngas reactor may vary depending on the carbon source, and may be operated at a pressure from 0 bar to 20 bar, e.g., from 1 bar to 15 bar.

Upon exiting syngas reactor 104, product gas 106 is preferably directly fed to carbonylation unit 108. In one embodiment, there is no separation of the hydrogen and carbon monoxide in the product gas prior to the carbonylation unit.

In some embodiments, depending on the carbon feedstock for gasification, the product gas, such as coal gas, may be treated to remove sulfur, tar and/or volatile matter. Tars may be reduced by using a catalyst in the gasification process, such as dolomite. Tars and phenolic hydrocarbons produced in a gasifier may require removal to reduce emissions, avoid fouling, and avoid poisoning catalysts in the integrated process. As compared to coal, biomass has a larger amount of total volatile matter, such as phenolics. During gasification, the volatile matter is released at relatively low temperatures. For example, a large part of this volatile material is responsible for the tar formation during gasification of biomass. Tar levels in the syngas also depend largely on the gasifier configuration. In an updraft fixed bed gasifier operated from 300° C. to 1000° C., the product gas may contain up to 3.5 wt. % tar when not controlled. Tars have relatively high heat contents and can be burned in combustors, but they may plug char filters and may form soot during combustion. Therefore, to maximize system efficiency, the tar may optionally be removed from the gasified biomass. Tar may be removed from the gasified biomass product through a catalytic tar reformer or thermal tar cracker. The catalytic tar reformer may be operated at a temperature comparable to the gasifier temperature, preferably below 900° C. However, the temperature should not drop below the tar dew point of about 540° C.

After gasification and optional tar removal, the product gas will be partially cooled to minimize the amount of alkali vapors. The cooling may occur at a temperature from 350° C. to 650° C. Optionally, the product may then pass through a filter to remove solids. A downstream of steam may be purged from the system or recycled to the gasifier.

Also, in some embodiments, the WGSR may be used to promote the ratio of hydrogen to carbon monoxide, in particular to recycle carbon dioxide from process vent/purge streams to produce additional carbon monoxide. This conversion may be accomplished in the syngas reactor directly or in a separate water gas shift reactor. After the WGSR, the product gas may comprise a $H_2$ to CO ratio that is greater than 1.8:1, e.g., greater than 1.9:1. In terms of ranges, the $H_2$ to CO ratio may be from 1.8:1 to 4:1, e.g., from 1.9:1 to 3:1.

As indicated above, carbon dioxide may be removed from product gas 106 to produce highly purified syngas stream 107. Upon exiting the gasifier, the product gas may have a carbon dioxide concentration from 0.5 to 25 mol. % carbon dioxide, e.g., from 2 to 15 mol. % carbon dioxide or from 5 to 10 mol. % carbon dioxide. In one embodiment, product gas 106 may be separated into a carbon dioxide stream 109 and a highly purified syngas stream 107. To accomplish this, the product gas may be fed to an acid gas removal device 105 that uses a solvent to remove acid gas, e.g., carbon dioxide. Solvents may include methanol, dimethyl ether of polyethylene glycol (DEPG), N-methyl-2-pyrrolidone (NMP), N-methyl-diethanolamine (MDEA), and propylene carbonate. A suitable acid gas removal process is the RECTISOL™ process developed by Lurgi. This process uses methanol as a solvent to remove sulfur and sulfur containing compounds such as hydrogen sulfide gas. The process also removes carbon dioxide. The methanol solvent may remove contaminants from the syngas, including ammonia, mercury and hydrogen cyanide. Once removed carbon dioxide stream 109 may be recycled to syngas reactor 104 as needed.

Other methods of removing carbon dioxide may include chemical solvents, physical solvents, membranes, and cryogenic fractionation. A membrane may be used when the product gas is at a higher pressure and contains large concentrations of carbon dioxide.

Carbonylation Unit

The product gas 106 that contains carbon monoxide, hydrogen and carbon dioxide is fed to carbonylation unit 108 and reacted with methanol reactant 118, such as methanol or a reactive derivative thereof, to produce acetic acid. In some embodiments, the carbon dioxide can be significantly separated from the syngas prior to feeding the syngas to the carbonylation reactor and then the carbon dioxide can be recycled to the syngas reactor to form additional carbon monoxide via the WGSR. As shown in FIG. 2, syngas 107 that contains carbon monoxide and hydrogen is fed to carbonylation unit 108 and reacted with methanol reactant 118, such as methanol or a reactive derivative thereof, to produce acetic acid.

Carbonylation processes for acetic acid from methanol are widely known in the art, and are further described in U.S. Pat. Nos. 3,769,329; 4,994,608; 5,001,259; 5,625,095, 5,763,654; 5,877,348; 7,005,541; and 7,678,940, the entire contents and disclosure of which is hereby incorporated by reference. In some embodiments, the product gas or syngas may be fed to a carbonylation unit that co-produces acetic acid and acetic anhydride. Acetic anhydride may be produced from methyl acetate. It is noted that U.S. Pat. No. 4,994,608 describes introducing 0.3 mol. % to 10 mol. % hydrogen into the carbonylation unit. The low level of hydrogen is used to achieve improved reaction rates. However, the low level of hydrogen is below that of the product gas of the present invention. In addition, U.S. Pat. No. 4,994,608 introduces carbon monoxide with a minor amount of hydrogen and does not introduce a product gas or syngas directly into the carbonylation unit.

The carbonylation reaction may be conducted in a homogeneous catalytic reaction system comprising a reaction solvent, methanol and/or reactive derivatives thereof, a promoter, a Group VIII catalyst, at least a finite concentration of water, and optionally a catalyst stabilizer/co-promoter, such as an iodide salt.

Suitable catalysts include Group VIII catalysts, e.g., rhodium and/or iridium catalysts. When a rhodium catalyst is utilized, the rhodium catalyst may be added in any suitable form such that the active rhodium catalyst is a carbonyl iodide complex. Exemplary rhodium catalysts are described in Michael Gauβ, et al., *Applied Homogeneous Catalysis with Organometallic Compounds: A Comprehensive Handbook in Two Volume*, Chapter 2.1, p. 27-200, (1$^{st}$ ed., 1996), the entirety of which is hereby incorporated by reference. Iodide salts optionally maintained in the reaction mixtures of the processes described herein may be in the form of a soluble salt of an alkali metal or alkaline earth metal or a quaternary ammonium, or in the form of a phosphonium salt. In certain embodiments, a catalyst co-promoter comprising lithium iodide, lithium acetate, or mixtures thereof may be employed. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; and 5,144,068, which are hereby incorporated by reference.

When an iridium catalyst is used, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]H^+$, $[Ir(CH_3)I_3(CO)_2]^-H^+$, $Ir_4(CO)_{12}$, $IrCl_3.3H_2O$, $IrBr_3.3H_2O$, $Ir_4(CO)_{12}$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $[H_2IrCl_6]$. Chloride-free complexes of iridium such as acetates, oxalates and acetoacetates are usually employed as starting materials. The iridium catalyst concentration in the liquid reaction composition may be in the range of 100 to 6000 ppm. The carbonylation of methanol using iridium catalyst is generally described in U.S. Pat. Nos. 5,942,460; 5,932,764; 5,883,295; 5,877,348; 5,877,347; and 5,696,284, which are hereby incorporated by reference.

In one embodiment the carbonylation catalyst does not comprise phosphorus containing ligands, such as diphosphine ligands or phosphoric acid triamide ligands. Without being bound by theory, it is believed that these phosphorus-containing ligands may lead to the formation of higher acids, such as propionic, butyric, valeric, and hexanoic acids. As described by Tempesti, et al., "Carboxylic acids by methanol carbonylation with syngas using polymer-supported rhodium catalysts," Reactive & Functional Polymers 33 (1997) 211-216, feeding syngas with methanol would also produce higher acids by the formula: $MeOH+2nH2+(n+1)CO \rightarrow Me(CH_2)_nCO_2H+nH_2O$.

A halogen co-catalyst/promoter is generally used in combination with the Group VIII metal catalyst component. Methyl iodide is a preferred halogen promoter. Preferably, the concentration of halogen promoter in the reaction medium ranges from 1 wt. % to 50 wt. %, and preferably from 2 wt. % to 30 wt. %.

The halogen promoter may be combined with the salt catalyst stabilizer/co-promoter compound. Particularly preferred are iodide or acetate salts, e.g., lithium iodide or lithium acetate.

Other promoters and co-promoters may be used as part of the catalytic system of the present invention as described in U.S. Pat. No. 5,877,348, which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 wppm.

In one embodiment, the temperature of the carbonylation reaction in the reactor is preferably from 150° C. to 250° C., e.g., from 160° C. to 225° C., or from 180° C. to 220° C. The pressure of the carbonylation reaction is preferably from 15 atm to 60 atm, and more preferably 20 atm to 40 atm. In the absence of water, and when using catalysts for bidentate phosphorus ligands at low temperatures and higher pressure, the carbonylation reaction may form acetaldehyde and/or ethanol predominantly instead of acetic acid. Moloy and Wegman, "Rhodium-Catalyzed Reductive Carbonylation of Methanol," Reductive Carbonylation of Methanol, July/August 1990, pages 353-356, disclose 80% selectivity to aldehyde using rhodium-diphosphine complexes at temperatures from 130° C. to 150° C. and pressure of about 70 atm. Acetic acid is typically manufactured in a liquid phase reaction at a temperature from 150° C. to 200° C. and a total pressure from 15 atm to 60 atm. The carbonylation liquid phase reaction is conducted in the presence of water that may also reduce impurities. Acetic anhydride may be produced in the liquid phase at higher temperature and/or pressures, such as from 140° C. to 250° C., preferably 180° C. to 220° C., and a total pressure from 30 atm to 70 atm, preferably from 40 atm to 60 atm. Without being bound by theory, in the presence of water, methanol carbonylation predominates with high methanol selectivity to acetic acid instead of to higher alcohols and acids, even at higher hydrogen partial pressure, because the rate of reductive elimination to acetyl iodide with concomitant hydrolysis of acetyl iodide to acetic acid is very rapid, such that the reaction of hydrogen iodide or hydrogen with the acyl rhodium carbonyl iodide complex is essentially eliminated.

In one embodiment, the reaction mixture comprises a reaction solvent or mixture of solvents. The solvent is preferably compatible with the catalyst system and may include pure alcohols, mixtures of an alcohol feedstock, and/or the desired carboxylic acid and/or esters of these two compounds. In one embodiment, the solvent and liquid reaction medium for the (low water of less than 14 wt. %) carbonylation process is preferably acetic acid.

Water may be formed in situ in the reaction medium, for example, by the esterification reaction between methanol reactant and acetic acid product. In some embodiments, water is introduced to the reactor together with or separately from other components of the reaction medium. Water may be separated from the other components of the reaction product withdrawn from the reactor and may be recycled in controlled amounts to maintain the required concentration of water in the reaction medium. Preferably, the concentration of water maintained in the reaction medium ranges from 0.1 wt. % to 14 wt. %, e.g., from 1 wt. % to 8 wt. %, or from 1 wt. % to 3 wt. % of the total weight of the reaction product. When producing acetic anhydride, the reaction medium is essentially anhydrous.

The desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present simultaneously. The absolute concentration of iodide ion content is not a limitation on the usefulness of the present invention.

In low water carbonylation, the additional iodide over and above the organic iodide promoter may be present in the catalyst solution in amounts ranging from 2 wt. % to 20 wt. %, e.g., from 2 wt. % to 15 wt. %, or from 3 wt. % to 10 wt. %; the methyl acetate may be present in amounts ranging from 0.5 wt. % to 30 wt. %, e.g., from 1 wt. % to 25 wt. %, or from 2 wt. % to 20 wt. %; and for lithium iodide as the additional iodide may be present in amounts ranging from 5 wt. % to 20 wt %, e.g., from 5 wt. % to 15 wt. %, or from 5 wt. % to 10 wt. %. The catalyst may be present in the catalyst solution in amounts ranging from 200 wppm to 2000 wppm, e.g., from 200 wppm to 1500 wppm, or from 500 wppm to 1500 wppm.

The carbonylation reactor is typically either a stirred vessel or bubble-column type within which the reacting liquid or slurry contents are maintained automatically at a constant level. Into this reactor, fresh methanol, product gas or syngas that contains hydrogen and carbon oxides, and sufficient water are continuously introduced as needed to maintain at least a finite concentration of water in the reaction medium. Several recycle streams are also introduced into the reactor.

Due to the excess hydrogen in the product gas or sygnas, the partial pressure of hydrogen in the reaction may be greater than 0.3 atm partial pressure of hydrogen. In terms of ranges, the hydrogen partial pressure may be from 3 to 40 atm, e.g., from 5 to 25 atm, or from 10 to 20 atm. The temperature of the reactor is controlled and the product gas or sygnas comprising primarily carbon monoxide and hydrogen is introduced at a rate sufficient to maintain the desired total reactor pressure. In some embodiments, the carbon monoxide partial pressure may be less than the hydrogen partial pressure. The carbon monoxide partial pressure in the reactor preferably is greater than 0.3 atm, e.g., greater than 1 atm, or greater than 3 atm. In general, the carbon monoxide partial pressure in the reactor may be less than 15 atm, e.g., less than 10 atm or less than 5 atm. In some embodiments, there is no upper limit on partial pressure of carbon monoxide and it may be preferable to operate the reactor at the highest carbon monoxide partial pressure possible to maintain catalyst stability. Generally, the carbon monoxide partial pressure may range from 0.3 to 30 atm, e.g., from 1 to 15 atm, or from 3 to 6 atm.

Vent Gas

Reactor vent gas 110 is desirably vented from the carbonylation reactor 108 to recover hydrogen and to purge other noncondensable gases such as nitrogen, carbon dioxide to maintain a set carbon monoxide partial pressure at a given total reactor pressure. Also a portion of the gases in the reactor are directed to the flasher from the reactor flash medium as dissolved and entrained gases. This portion of gases can combine with the reactor vent noncondensable gases or can combine with the vent via the carbonylation unit low pressure scrubber vent of the purification section 112. The reactor vent gas may comprise at least one non-condensable gas such as hydrogen, carbon dioxide, carbon monoxide, nitrogen, and mixtures thereof. The reactor vent gas 110 may be enriched in hydrogen as compared to product gas 106 or syngas 107. Most of the carbon monoxide from the product gas is consumed in the carbonylation reaction. In one embodiment, the reactor vent gas may comprise from 5 mol. % to 95 mol. % hydrogen, e.g., from 10 mol. % to 90 mol. % or from 35 mol. % to 85 mol. %. Also, vent gas may comprise 4 mol. % to 70 mol. % carbon dioxide, e.g., from 5 mol. % to 70 mol. %, from 10 mol. % to 35 mol. % or from 15 mol. % to 25 mol. %. In some embodiments, reactor vent gas 110 may be withdrawn via reactor vent 135.

Hydrogen from the reactor vent gas may be used in several processes, such as for hydrocracking of heavy petroleum fractions or used to produce ammonia via the Haber process. In another embodiment as shown in FIG. 2 and described further herein, hydrogen may be used in hydrogenation processes to convert acetic acid to ethanol, as described in U.S. Pat. Nos. 7,608,744 and 7,863,489, the entire contents and disclosure of which is hereby incorporated by reference. For example, the acetic acid produced by the carbonylation may be converted to ethanol using the recovered hydrogen in the vent gas. Depending on the carbon dioxide and carbon monoxide concentrations and end use of the products, the hydrogen can be easily purified further to remove residue low levels of carbon dioxide and carbon monoxide from the vent gas as needed. In one embodiment, vent gas 110 may be fed to an acid gas removal device 120 using a solvent as described above. A stream 122 enriched in carbon dioxide may be removed from vent gas 110 and the remaining vent gas 124 is directed to a hydrogen removal device 126. For example a hydrogen permeable membrane, molecular sieves, or pressure swing adsorption (PSA) may also be used to obtain a hydrogen stream having a high purity of greater than 99.9%. Pd-composite membrane may be suitable for providing high hydrogen permeability. In one embodiment the purified hydrogen may be used for fuel cells to produce electricity. The hydrogen removal device 126 produces an enriched hydrogen stream 128 and a carbon monoxide stream 130 which is significantly more economical than separating the hydrogen from product gas 106 or syngas 107 prior to carbonylation reactor 108. Hydrogen 128 that is recovered from reactor vent gas 110 is combined with the produced acetic acid, either in lines 114 or 116, to form ethanol 146 as shown in FIG. 2.

The carbon dioxide may be used to produce several other chemical processes or used within the carbonylation or syngas process. For example, the carbon dioxide that is recovered from the vent gas may be recycled to the syngas reactor, or a separate water gas shift reactor. In addition, carbon dioxide may be sequestered to reduce the amount of greenhouse gases or used in enhanced oil recovery process. In one embodiment, when the carbon source is biomass, the recovered carbon dioxide may be used to dry the biomass in the pre-processing steps.

In one embodiment, when venting the hydrogen and carbon dioxide, a portion of carbon monoxide may also be vented. Generally, the reactor vent gas comprises less carbon monoxide, based on mole percent, than the product gas. Thus, the reactor vent gas may further comprise from 0.2 mol. % to 40 mol. % carbon monoxide, e.g., from 0.2 mol. % to 20 mol. %, from 1 mol. % to 15 mol. % or from 5 mol. % to 10 mol. %. To maximize carbon monoxide efficiency when producing acetic acid, it is preferable to recover the carbon monoxide from the vent gas and recycle the carbon monoxide with or without residual hydrogen and carbon dioxide to the carbonylation reactor directly or via the syngas reactor. In addition it is preferable to treat the reactor vent gas to reduce the carbon monoxide content to less than 1 mol. % or less than 0.1 mol. %. Carbon monoxide may be separated before or after separating the carbon dioxide from the vent gas, as needed. In one embodiment, a portion of the carbon monoxide vent stream from the reactor vent and/or from the purification section vent may be scrubbed using acetic acid and/or methanol, and returned to the carbonylation unit directly or via the syngas reactor. For example, the returned carbon monoxide vent stream may be used to stabilize the catalyst in the flasher, pump suction lines of the flasher and reactor recycle pumps, and heat exchangers associated with the flasher and reactor.

The residual carbon monoxide in the vent gas may be further reduced, if desired, by reacting in a vapor phase carbonylation reaction, or secondary carbonylation reactor, using a heterogeneous catalyst, as described U.S. Pat. No. 8,394,988, the entire contents and disclosure of which is incorporated by reference. A similar Group VIII metal catalyst may be used in the vapor phase carbonylation reaction. Thus, additional acetic acid may be produced from the carbon monoxide in the reactor vent gas and further increase the yield to acetic acid.

In other embodiments, the residual carbon monoxide in the vent gas may be further reduced, if desired using gas purification processes know in the art such as pressure swing absorption, membrane separation, cryogenic separation and the like prior to a removal of residual carbon dioxide if necessary using an acid gas removal device. In addition, acid gas removal device may be used to remove carbon dioxide, either after carbon monoxide removal or alone.

Acetic Acid Recovery

A liquid product is drawn off from the carbonylation reactor 108 at a rate sufficient to maintain a constant level therein and is introduced to the flasher. In the flasher, a catalyst-containing solution (catalyst phase) is withdrawn as a base stream (predominantly acetic acid containing the rhodium and the iodide salt along with lesser quantities of methyl acetate, methyl iodide, and water), while a vapor stream 111, also referred to as a crude product, comprising acetic acid is withdrawn overhead. The vapor stream 111 may comprise acetic acid, methyl iodide, methanol, methyl acetate, water, and mixtures thereof. The amount of methyl acetate may vary and, in some embodiments, the crude product may have less than 25 wt. % methyl acetate. In other embodiments, the amount of methyl acetate may be more than 25 wt. %. In addition the vapor stream may comprise one or more permanganate reducing compounds (PRC) selected from the group consisting of acetaldehyde, acetone, methyl ethyl ketone, butyraldehyde, crotonaldehyde, 2-ethyl crotonaldehyde, 2-ethyl butyraldehyde and the like, and the aldol condensation products thereof. Without being bound by theory, the concentration of PRC may be increased due to the excess hydrogen in the product gas. In addition to PRC, heavier acids may also form, such as propionic acid. Propionic acid, if present in undesirable levels of greater than 0.5 wt. %, may be separated from the acetic acid. In some embodiments, the vapor stream may comprise from 0.1 wt. % to 5 wt. %, e.g., from 0.1 to 3 wt. %, or 0.2 wt. % to 0.8 wt. %, of a mixture of ethanol and/or propionic acid.

Recovery of acetic acid from the vapor stream 111 may be accomplished using several different processes of distillation and purification 112. In one exemplary process for recovering acetic acid, the vapor stream is fed to a light ends column. The light ends column yields a low-boiling overhead vapor stream, a product side stream, and an optional bottoms stream. The optional bottoms stream may comprise entrained catalyst. The temperature at the base of the light ends column, i.e., temperature of optional bottoms stream, preferably is from 120° C. to 170° C. In addition, the temperature at the top of the light ends column, i.e., temperature of low-boiling overhead vapor stream, preferably is from 100° C. to 145° C.

The low-boiling overhead vapor stream may comprise methyl iodide, methyl acetate, water, PRC, acetic acid, alkanes, and dissolved gases. The low-boiling overhead vapor stream may be condensed and directed to an overhead phase separation unit, such as a decanter. Conditions are desirably maintained such that the condensed low-boiling overhead vapor stream, once in decanter, will separate into a light phase and a heavy phase.

The light phase may comprise water, acetic acid, and PRC, as well as methyl iodide and methyl acetate. The light phase may be refluxed, as needed, to the light ends column. In one embodiment, the light phase may also be separated and processed in a PRC recovery system (PRS) to remove PRC. Suitable PRS's are described in U.S. Pat. Nos. 7,855,306; 7,223,886; and 6,143,930, and US Pub. No. 2012/0090981, which are hereby incorporated by reference. Also a portion of the light phase may be returned to the carbonylation reactor.

The heavy phase from the decanter can be conveniently recirculated, either directly or indirectly, to the reactor.

The product side stream from the light ends column comprises primarily acetic acid and water. The product side stream preferably is in the liquid phase and is withdrawn from the light ends column at a temperature from 115° C. to 160° C., e.g., from 125° C. to 155° C. A drying column may separate the product side stream to yield an overhead stream, comprised primarily of water, and a dried purified product stream 116. The dried purified product stream 116 preferably comprises acetic acid in an amount greater than 90 wt. %, e.g., greater than 95 wt. % or greater than 98 wt. %. The temperature at the base of the drying column, i.e., temperature of the exiting dried purified product stream, preferably is from 130° C. to 185° C., e.g., 140° C. to 180° C. or 150° C. to 175° C. The temperature at the top of drying column, i.e., temperature of the overhead stream, preferably is from 110° C. to 150° C., e.g., 120° C. to 150° C. or 130° C. to 145° C. In some embodiments, the pressure in the drying column is from 2 bar to 7 bar, e.g., 3 bar to 6 bar, or 4 bar to 5 bar. Optionally, the dried purified product stream 116 and the acetic acid with impurities 114 such as aldehydes and/or propanoic acid may be further treated in one or more guard beds and/or heavy ends columns to further remove impurities, such as halides, or heavier acids, such as propionic acid, and/or esters.

The overhead stream from the drying column may be cooled and condensed in an overhead receiver. In some embodiments, the overhead stream may be phased and the light phase is refluxed to the drying column. The remaining portion of the overhead stream, either light or heavy phase, may be returned to the carbonylation reactor.

In another embodiment, one or more vent gas streams 132 may be obtained during the recovery of acetic acid. For example, vent gas from the decanter of the light ends column may be combined with the reactor vent gas 110 via optional line 133. This allows any hydrogen that passes through with the vapor stream of the flasher to be captured and separated. In addition, any carbon monoxide in the vent gas may be recovered to be converted into additional acetic acid. Vent gas stream 132 may also be purged as purification vent 134.

Hydrogenation Unit

As shown in FIG. 2, hydrogen recovered from the vent gas and acetic acid produced from the carbonylation separation unit 112 may be co-fed to hydrogenation unit 140 to produce ethanol. Depending on the purification in unit 112, a purified acetic acid stream may be fed to hydrogenation unit 140 or a stream that comprises acetic acid and impurities, such as methyl acetate, anhydride, acetaldehyde, propionic acid, and mixtures thereof, may be fed to hydrogenation unit. A portion of the acetic acid may be integrated with the hydrogenation unit 140 and another portion of the acetic acid separated as an additional product. For the purposes of the present invention, the exemplary hydrogenation process will be described in terms of acetic acid, but it is also applicable to acetic anhydride.

The acetic acid fed to the hydrogenation reactor may also comprise other carboxylic acids, esters, and anhydrides, as well as aldehydes and/or ketones, such as acetaldehyde and acetone. Preferably, a suitable acetic acid feed stream comprises one or more of the compounds selected from the group consisting of acetic acid, acetic anhydride, acetaldehyde, ethyl acetate, and mixtures thereof. These other compounds may also be hydrogenated in the processes of the present invention. In some embodiments, the presence of carboxylic acids, such as propanoic acid or its anhydride, may be beneficial in producing propanol. Water may also be present in the acetic acid feed.

The acetic acid may be vaporized at the reaction temperature, following which the vaporized acetic acid may be fed along with hydrogen in an undiluted state or diluted with a relatively inert carrier gas, such as nitrogen, argon, helium, carbon dioxide and the like. For reactions run in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature. Preferably, the acetic acid is transferred to the vapor state by passing hydrogen and/or recycle gas through the acetic acid at a temperature at or below 125° C., followed by heating of the combined gaseous stream to the reactor inlet temperature.

In preferred embodiments, the catalyst is employed in a fixed bed reactor, e.g., in the shape of a pipe or tube, where the reactants, typically in the vapor form, are passed over or through the catalyst. Other reactors, such as fluid or ebullient bed reactors, can be employed. In some instances, the hydrogenation catalysts may be used in conjunction with an inert material to regulate the pressure drop of the reactant stream through the catalyst bed and the contact time of the reactant compounds with the catalyst particles.

The hydrogenation in the reactor may be carried out in either the liquid phase or vapor phase. Preferably, the reaction is carried out in the vapor phase under the following conditions. The reaction temperature may range from 125° C. to 350° C., e.g., from 200° C. to 325° C., from 225° C. to 300° C., or from 250° C. to 300° C. The hydrogenation reactor pressure may range from 10 kPa to 3000 kPa, e.g., from 50 kPa to 2300 kPa, or from 100 kPa to 1500 kPa. The reactants may be fed to the reactor at a gas hourly space velocity (GHSV) of greater than 500 $hr^{-1}$, e.g., greater than 1000 $hr^{-1}$, greater than 2500 $hr^{-1}$ or even greater than 5000 $hr^{-1}$. In terms of ranges the GHSV may range from 50 $h^{-1}$ to 50,000 $hr^{-1}$, e.g., from 500 $hr^{-1}$ to 30,000 $hr^{-1}$, from 1000 $hr^{-1}$ to 10,000 $hr^{-1}$, or from 1000 $hr^{-1}$ to 6500 $hr^{-1}$.

The hydrogenation optionally is carried out at a pressure just sufficient to overcome the pressure drop across the catalytic bed at the GHSV selected, although there is no bar to the use of higher pressures, it being understood that considerable pressure drop through the reactor bed may be experienced at high space velocities, e.g., 5000 $hr^{-1}$ or 6,500 $hr^{-1}$.

Although the reaction consumes two moles of hydrogen per mole of acetic acid to produce one mole of ethanol, the actual molar ratio of hydrogen to acetic acid in the feed stream may vary from about 100:1 to 1:100, e.g., from 50:1 to 1:50, from 20:1 to 1:2, or from 18:1 to 2:1. Most preferably, the molar ratio of hydrogen to acetic acid is greater than 2:1, e.g., greater than 4:1 or greater than 8:1. In some embodiments, additional hydrogen not recovered from the vent gas may be used in increase the hydrogen to acetic acid ratio as needed.

Contact or residence time can also vary widely, depending upon such variables as amount of acetic acid, catalyst, reactor, temperature, and pressure. Typical contact times range from a fraction of a second to more than several hours when a catalyst system other than a fixed bed is used, with preferred contact times, at least for vapor phase reactions, from 0.1 to 100 seconds, e.g., from 0.3 to 80 seconds or from 0.4 to 30 seconds.

The hydrogenation of acetic acid to form ethanol is preferably conducted in the presence of a hydrogenation catalyst in the reactor. In one embodiment, the hydrogenation catalyst may be a bifunctional catalyst and may convert acetic acid and ethyl acetate. The catalysts preferably are not methanol synthesis catalysts and are substantially free of copper and/or zinc, including oxides thereof. Suitable hydrogenation catalysts include catalysts comprising a first metal and optionally one or more of a second metal, a third metal or any number of additional metals, optionally on a catalyst support. Preferred bimetallic combinations for some exemplary catalyst compositions include platinum/tin, platinum/ruthenium, platinum/rhenium, palladium/ruthenium, palladium/rhenium, cobalt/palladium, cobalt/platinum, cobalt/chromium, cobalt/ruthenium, cobalt/tin, silver/palladium, nickel/palladium, gold/palladium, ruthenium/rhenium, and ruthenium/iron. Additional metal combinations may include palladium/rhenium/tin, palladium/rhenium/cobalt, palladium/rhenium/nickel, platinum/tin/palladium, platinum/tin/cobalt, platinum/tin/chromium, and platinum/tin/nickel. Exemplary hydrogenation catalysts are further described in U.S. Pat. Nos. 7,608,744 and 7,863,489, and 8,471,075, the entireties of which are incorporated herein by reference. In another embodiment, the catalyst comprises a Co/Mo/S catalyst of the type described in U.S. Pat. No. 7,923,405, the entirety of which is incorporated herein by reference.

In one embodiment, the hydrogenation catalyst comprises a first metal selected from the group consisting of copper, iron, cobalt, nickel, ruthenium, rhodium, palladium, osmium, iridium, platinum, titanium, zinc, chromium, rhenium, molybdenum, and tungsten. The first metal may be selected from the group consisting of platinum, palladium, cobalt, nickel, and ruthenium. More preferably, the first metal is platinum or palladium. In embodiments of the invention where the first metal comprises platinum, it is preferred that the catalyst comprises platinum in an amount less than 5 wt. %, e.g., less than 3 wt. % or less than 1 wt. %, due to the high demand for platinum.

As indicated above, in some embodiments, the catalyst further comprises a second metal, which typically would function as a promoter. If present, the second metal preferably is selected from the group consisting of copper, molybdenum, tin, chromium, iron, cobalt, vanadium, tungsten, palladium, platinum, lanthanum, cerium, manganese, ruthenium, rhenium, gold, and nickel. The second metal may be selected from the group consisting of copper, tin, cobalt, rhenium, and nickel. More preferably, the second metal is tin or rhenium.

In one embodiment, the one or more active metals comprise a first metal selected from the group consisting of copper, iron, cobalt, nickel, ruthenium, rhodium, platinum, palladium, osmium, iridium, titanium, zinc, chromium, rhenium, molybdenum and tungsten. The one or more active metals may further comprise a second metal selected from the group consisting of copper, molybdenum, tin, chromium, iron, cobalt, vanadium, tungsten, palladium, platinum, lanthanum, cerium, manganese, ruthenium, rhenium, gold, and nickel. Preferably, the second metal is different than the first metal.

In certain embodiments where the hydrogenation catalyst includes two or more metals, e.g., a first metal and a second metal, the first metal is present in the catalyst in an amount from 0.1 to 10 wt. %, e.g., from 0.1 to 5 wt. %, or from 0.1 to 3 wt. %. The second metal preferably is present in an amount from 0.1 to 20 wt. %, e.g., from 0.1 to 10 wt. %, or from 0.1 to 5 wt. %. For catalysts comprising two or more metals, the two or more metals may be alloyed with one another or may comprise a non-alloyed metal solution or mixture.

The preferred metal ratios may vary depending on the metals used in the catalyst. In some exemplary embodiments, the molar ratio of the first metal to the second metal is from 10:1 to 1:10, e.g., from 4:1 to 1:4, from 2:1 to 1:2, from 1.5:1 to 1:1.5 or from 1.1:1 to 1:1.1.

The catalyst may also comprise a third metal selected from any of the metals listed above in connection with the first or second metal, so long as the third metal is different from the first and second metals. In preferred aspects, the third metal is selected from the group consisting of cobalt, palladium, ruthenium, copper, zinc, platinum, tin, and rhenium. More preferably, the third metal is selected from cobalt, palladium, and ruthenium. When present, the total weight of the third metal preferably is from 0.05 to 7.5 wt. %, e.g., from 0.1 to 5 wt. %, or from 0.1 to 3 wt. %.

In addition to the one or more metals, in some embodiments the catalysts further comprise a support or a modified support. As used herein, the term "modified support" refers to a support that includes a support material and a support modifier, which adjusts the acidity of the support material.

The total weight of the support or modified support, based on the total weight of the catalyst, preferably is from 75 to 99.9 wt. %, e.g., from 78 to 97 wt. %, or from 80 to 95 wt. %. In preferred embodiments that utilize a modified support, the support modifier is present in an amount from 0.1 to 50 wt. %, e.g., from 0.2 to 25 wt. %, from 0.5 to 15 wt. %, or from 1 to 8 wt. %, based on the total weight of the catalyst. The metals of the catalysts may be dispersed throughout the support, layered throughout the support, coated on the outer surface of the support (i.e., egg shell), or decorated on the surface of the support.

As will be appreciated by those of ordinary skill in the art, support materials are selected such that the catalyst system is suitably active, selective and robust under the process conditions employed for the formation of ethanol.

Suitable support materials may include, for example, stable metal oxide-based supports or ceramic-based supports. Preferred supports include silicaceous supports, such as silica, silica/alumina, a Group IIA silicate such as calcium metasilicate, pyrogenic silica, high purity silica, and mixtures thereof. Other supports may include, but are not limited to, iron oxide, alumina, titania, zirconia, magnesium oxide, carbon, graphite, high surface area graphitized carbon, activated carbons, and mixtures thereof.

In preferred embodiments, the support is selected from the group consisting of silica, silica/alumina, calcium metasilicate, pyrogenic silica, high purity silica, carbon, alumina, and mixtures thereof.

As indicated, the catalyst support may be modified with a support modifier. In some embodiments, the support modifier may be an acidic modifier that increases the acidity of the catalyst. Suitable acidic support modifiers may be selected from the group consisting of: oxides of Group IVB metals, oxides of Group VB metals, oxides of Group VIB metals, oxides of Group VIIB metals, oxides of Group VIIIB metals, aluminum oxides, and mixtures thereof. Acidic support modifiers include those selected from the group consisting of $TiO_2$, $ZrO_2$, $Nb_2O_5$, $Ta_2O_5$, $Al_2O_3$, $B_2O_3$, $P_2O_5$, and $Sb_2O_3$. Preferred acidic support modifiers include those selected from the group consisting of $TiO_2$, $ZrO_2$, $Nb_2O_5$, $Ta_2O_5$, and $Al_2O_3$. The acidic modifier may also include $WO_3$, $MoO_3$, $Fe_2O_3$, $Cr_2O_3$, $V_2O_5$, $MnO_2$, $CuO$, $Co_2O_3$, and $Bi_2O_3$.

In another embodiment, the support modifier may be a basic modifier that has low volatility or no volatility. Such basic modifiers, for example, may be selected from the group consisting of: (i) alkaline earth metal oxides, (ii) alkali metal oxides, (iii) alkaline earth metal metasilicates, (iv) alkali metal metasilicates, (v) Group IIB metal oxides, (vi) Group IIB metal metasilicates, (vii) Group IIIB metal oxides, (viii) Group IIIB metal metasilicates, and mixtures thereof. In addition to oxides and metasilicates, other types of modifiers including nitrates, nitrites, acetates, and lactates may be used. Preferably, the support modifier is selected from the group consisting of oxides and metasilicates of any of sodium, potassium, magnesium, calcium, scandium, yttrium, and zinc, as well as mixtures of any of the foregoing. More preferably, the basic support modifier is a calcium silicate, and even more preferably calcium metasilicate ($CaSiO_3$). If the basic support modifier comprises calcium metasilicate, it is preferred that at least a portion of the calcium metasilicate is in crystalline form.

The catalyst compositions suitable for use with the present invention preferably are formed through metal impregnation of the modified support, although other processes such as chemical vapor deposition may also be employed. Such impregnation techniques are described in U.S. Pat. Nos. 7,608,744, 7,863,489, and 8,471,075 referred to above, the entireties of which are incorporated herein by reference.

In some instances, the hydrogenation catalysts may be used in conjunction with an inert material to regulate the pressure drop of the reactant stream through the catalyst bed and the contact time of the reactant compounds with the catalyst particles.

In particular, the hydrogenation of acetic acid may achieve favorable conversion of acetic acid and favorable selectivity and productivity to ethanol in the reactor. For purposes of the present invention, the term "conversion" refers to the amount of acetic acid in the feed that is converted to a compound other than acetic acid. Conversion is expressed as a percentage based on acetic acid in the feed. The conversion may be at least 40%, e.g., at least 60%, or at least 80%. Higher conversions of greater than 90% may be required when the crude ethanol stream is contacted with the olefin feed stream. It is preferred to achieve very high conversion that approaches near 100% conversion.

Selectivity is expressed as a mole percent based on converted acetic acid. It should be understood that each compound converted from acetic acid has an independent selectivity and that selectivity is independent from conversion. For example, if 60 mole % of the converted acetic acid is converted to ethanol, the ethanol selectivity is referred to as 60%. In one embodiment, catalyst selectivity to ethanol is at least 60%, e.g., at least 70%, or at least 80%. Preferably, the selectivity to ethanol is at least 80%, e.g., at least 85% or at least 88%. Preferred embodiments of the hydrogenation process also have low selectivity to undesirable products, such as methane, ethane, and carbon dioxide. The selectivity to these undesirable products preferably is less than 4%, e.g., less than 2% or less than 1%. More preferably, these undesirable products are present in undetectable amounts. Formation of alkanes may be low, and ideally less than 2%, less than 1%, or less than 0.5% of the acetic acid passed over the catalyst is converted to alkanes, which have little value other than as fuel.

The term "productivity," as used herein, refers to the grams of a specified product, e.g., ethanol, formed during the hydrogenation based on the kilograms of catalyst used per hour. A productivity of at least 100 grams of ethanol per kilogram of catalyst per hour, e.g., at least 400 grams of ethanol per kilogram of catalyst per hour or at least 600 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

In various embodiments, the crude ethanol stream produced by the hydrogenation reactor typically comprises acetic acid, ethanol and water. In one embodiment, the crude ethanol stream may comprise from 5 to 72 wt. % ethanol, e.g., from 15 to 70 wt. % or from 25 to 65 wt. %, from 0 to 90 wt. % acetic acid, e.g., from 0 to 50 wt. % or from 0 to 35 wt. %, and from 5 to 40 wt. % water, e.g., from 5 to 30 wt. % water, or from 10 to 26 wt. %. There may be lower amounts of acetic acid when the conversion is higher. The crude ethanol produce may also comprise from 0 to 30 wt. % ethyl acetate, e.g., from 1 to 25 wt. % ethyl acetate, or from 5 to 18 wt. % ethyl acetate.

Returning to FIG. 2, an ethanol product 146 may be recovered from the crude ethanol product 142 produced by the hydrogenation unit 140 using the hydrogenation catalyst may be recovered using distillation and purification 144. Several different techniques are described in U.S. Pat. Nos. 8,309,773, 8,304,586, 8,304,587, and US Pub. Nos. 2012/0010438, 2012/0273338, 2012/0277490, 2012/0277497, or membranes as described in US Pub. No. 2012/0010445 the entire contents and disclosures of which are hereby incorporated by reference. Hydrogen in recyclable gas 148 may be treated as needed to remove carbon monoxide and/or carbon dioxide and returned to hydrogenation unit 140. Recyclable gas 148 may be purged via line 152 or directed to syngas reactor 104 via line 150.

The ethanol product may be an industrial grade ethanol comprising from 75 to 96 wt. % ethanol, e.g., from 80 to 96 wt. % or from 85 to 96 wt. % ethanol, based on the total weight of the ethanol product. The industrial grade ethanol may have a water concentration of less than 12 wt. % water, e.g., less than 8 wt. % or less than 3 wt. %. In some embodiments, when further water separation is used, the ethanol product preferably contains ethanol in an amount that is greater than 96 wt. %, e.g., greater than 98 wt. % or greater than 99.5 wt. %. The ethanol product having further water separation preferably comprises less than 3 wt. % water, e.g., less than 2 wt. % or less than 0.5 wt. %.

The finished ethanol composition produced by the embodiments of the present invention may be used in a variety of applications including fuels, solvents, chemical feedstocks, pharmaceutical products, cleansers, sanitizers, hydrogen transport or consumption. In fuel applications, the finished ethanol composition may be blended with gasoline for motor vehicles such as automobiles, boats and small piston engine aircraft. In non-fuel applications, the finished ethanol composition may be used as a solvent for toiletry and cosmetic preparations, detergents, disinfectants, coatings, inks, and pharmaceuticals. The finished ethanol composition may also be used as a processing solvent in manufacturing processes for medicinal products, food preparations, dyes, photochemicals and latex processing.

The finished ethanol composition may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, the finished ethanol composition may be esterified with acetic acid. In another application, the finished ethanol composition may be dehydrated to produce ethylene. Any known dehydration catalyst, such as zeolite catalysts or phosphotungstic acid catalysts, can be employed to dehydrate ethanol, as described in U.S. Pub. Nos. 2010/0030002 and 2010/0030001 and WO2010146332, the entire contents and disclosures of which are hereby incorporated by reference.

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

What is claimed is:

1. A process for producing acetic acid comprising:
    introducing a product gas comprising carbon monoxide, hydrogen, and carbon dioxide and at least one reactant selected from the group consisting of methanol, methyl acetate, methyl formate, dimethyl ether and mixtures thereof to a reactor comprising a reaction medium comprising a catalyst, methyl acetate, promoter, and catalyst stabilizer under carbonylation conditions effective to produce acetic acid, wherein hydrogen partial pressure in the reactor is from 3 atm to 40 atm;
    withdrawing a vent gas from the reactor, provided that the carbon monoxide partial pressure in the reactor is less than 15 atm to maintain a carbon monoxide content in the vent gas of less than 40 mol. %;
    withdrawing a reaction solution from the reactor; and
    recovering acetic acid from the reaction solution.

2. The process of claim 1, wherein the product gas has a hydrogen to carbon monoxide molar ratio of 0.2:1 to 6:1.

3. The process of claim 1, wherein the product gas has a carbon dioxide to carbon monoxide molar ratio from 1:0.5 to 1:80.

4. The process of claim 1, wherein the product gas comprises from 9 mol. % to 80 mol. % hydrogen, from 3 mol. % to 90 mol. % carbon monoxide, and from 0.5 mol. % to 25 mol. % carbon dioxide.

5. The process of claim 1, wherein carbon monoxide partial pressure in the reactor is from 0.3 atm to 15 atm.

6. The process of claim 1, wherein hydrogen partial pressure in the reactor is from 5 atm to 25 atm.

7. The process of claim 1, wherein carbon monoxide partial pressure in the reactor is less than hydrogen partial pressure in the reactor.

8. The process of claim 1, wherein the vent gas comprises from 5 mol. % to 95 mol. % hydrogen, and from 4 mol. % to 70 mol. % carbon dioxide, and from 0.2 mol. % to 40 mol. % carbon monoxide.

* * * * *